United States Patent [19]
Richard

[11] Patent Number: 5,205,128
[45] Date of Patent: * Apr. 27, 1993

[54] MULTICHAMBER STORAGE APPARATUS AND RELATED METHOD

[75] Inventor: Daniel D. Richard, Sedona, Ariz.

[73] Assignee: Cryo-Cell International, Inc., Baldwin, N.Y.

[*] Notice: The portion of the term of this patent subsequent to Jul. 9, 2008 has been disclaimed.

[21] Appl. No.: 726,841

[22] Filed: Jul. 8, 1991

Related U.S. Application Data

[63] Continuation-in-part of Ser. No. 535,414, Jun. 8, 1990, Pat. No. 5,029,447, and continuatioin-in-part of Ser. No. 670,979, Mar. 18, 1991.

[51] Int. Cl.⁵ .............................................. F25D 13/06
[52] U.S. Cl. ......................................... 62/63; 62/441
[58] Field of Search ............................ 62/63, 65, 441

[56] References Cited

U.S. PATENT DOCUMENTS

| | | |
|---|---|---|
| 1,938,985 | 12/1933 | Starr . |
| 2,599,173 | 6/1952 | Hamilton . |
| 2,928,705 | 3/1960 | Goldsmith . |
| 2,950,605 | 8/1960 | Hennion . |
| 3,034,845 | 5/1962 | Haumann . |
| 3,109,969 | 8/1963 | Elfving . |
| 3,141,123 | 7/1964 | Olson . |
| 3,564,727 | 2/1971 | Fraser . |
| 3,583,171 | 6/1971 | Flynn . |
| 3,696,631 | 10/1972 | Valdes . |
| 4,124,992 | 11/1978 | Chmiel . |
| 4,199,022 | 4/1980 | Senkan et al. . |
| 4,304,293 | 12/1981 | Scheiwe et al. . |
| 4,314,459 | 2/1982 | Rivoire . |
| 4,340,263 | 7/1982 | Webb . |
| 4,480,682 | 11/1984 | Kaneta et al. . |
| 4,531,373 | 7/1985 | Rubinsky . |
| 4,627,799 | 12/1986 | Terauchi . |
| 4,681,839 | 7/1987 | Swartz . |
| 4,712,607 | 12/1987 | Lindemans et al. . |
| 4,713,941 | 12/1987 | Toyoda et al. . |
| 4,790,141 | 12/1988 | Glascock . |
| 4,870,829 | 10/1989 | Oullette . |

Primary Examiner—Ronald C. Capossela
Attorney, Agent, or Firm—R. Neil Sudol; Henry D. Coleman

[57] ABSTRACT

A storage apparatus comprises a housing for defining a cryogenic storage unit and a plurality of low-temperature chambers disposed one next to the other, the housing including partitions for separating the chambers from one another. Temperature controls for controlling temperature independently in each of the chambers is operatively connected to each of the chambers. Each one of the chambers has access to at least one other chamber contiguous with the one chamber. Supports are provided for holding a plurality of specimens within each chamber A conveyor or transfer mechanism is provided for transfering selected specimens between contiguous chambers, independently of other specimens in the housing. In addition, access is provided to the housing to enable deposition and removal of given specimens from the housing. A plurality of individually operable freezing/thawing units are also connected to the cryogenic unit for controlling the freezing and thawing of specimens or groups of specimens at different freezing and thawing rates. The durations of temporary specimen storage in the low-temperature chambers and the rates of temperature change in the freezing/thawing chambers are controlled by a computer in accordance with pre-established freezing and heating protocols.

25 Claims, 10 Drawing Sheets

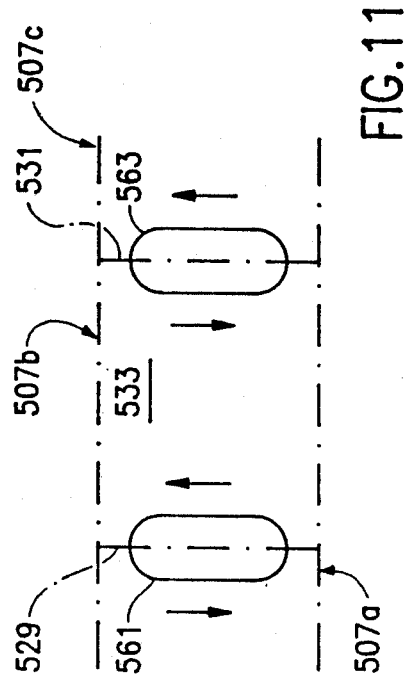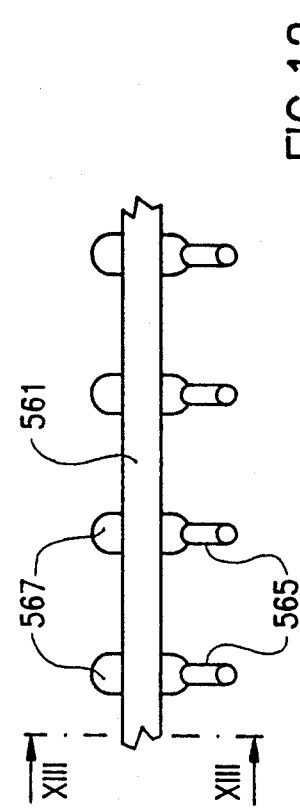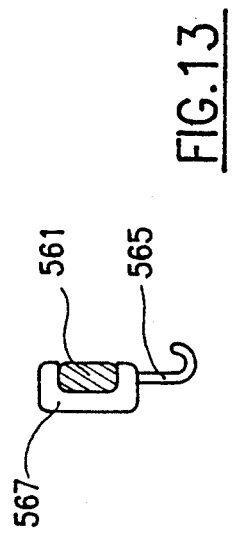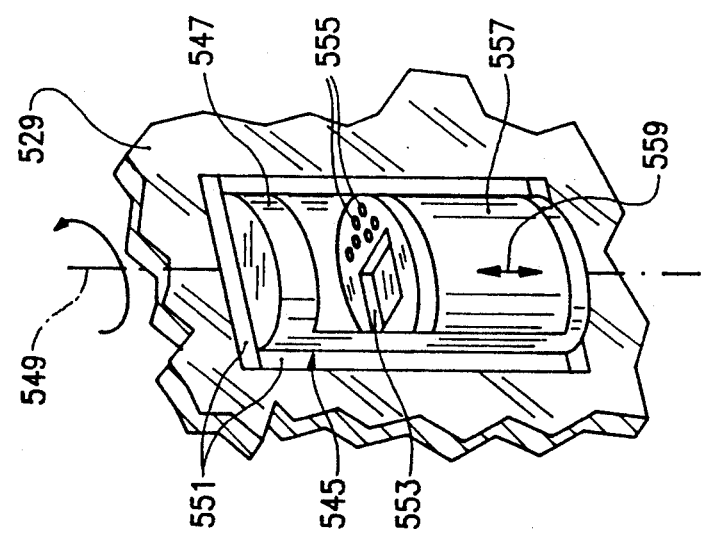

MULTICHAMBER STORAGE APPARATUS AND RELATED METHOD

CROSS-REFERENCE TO A RELATED APPLICATION

This application is a continuation-in-part of commonly owned application Ser. No. 535,414, filed Jun. 8, 1990, now U.S. Pat. No. 5,029,447. This application is also a continuation-in-part of commonly owned application Ser. No. 670,979 filed Mar. 18, 1991.

BACKGROUND OF THE INVNETION

This invention relates to a storage apparatus, particularly a low-temperature storage apparatus.

It is well known to use liquid nitrogen in the short-term and long-term storage of biological materials such as blood cells and micro-organisms. The storage is meant to preserve the biological integrity of cellular tissues and organisms for future therapeutic use and research.

Liquid nitrogen is used in part because it is has a relatively low boiling point. Owing to difficulties in manufacture, however, liquid nitrogen is a very expensive substance. Consequently, U.S. Pat. No. 5,029,447 described a storage apparatus having several chambers storing specimens at different temperatures. Specimens were moved from chamber to chamber, thereby maintaining viability of the stored specimens even though at any one time only a portion of the specimens were in a chamber at liquid nitrogen ternperatures. This design enables the use of coolants other than liquid nitrogen for at least some of the storage chambers, thereby reducing the storage expense.

It has been recognized that different types of biological specimens, namely different tissue types, have different optimum thawing and freezing rates or combinations of rates (protocols). U.S. patent application Ser. No. 670,979 describes a method and system for automatically freezing and thawing specimens which have such different rates or protocols. The system facilitates storage operations, particularly when many specimens are involved.

OBJECTS OF THE INVENTION

An object of the present invention is to provide an improved multichamber storage apparatus.

Another object of the present invention is to provide such a multichamber storage apparatus which takes into account the fact that different kinds of biological specimens have different optimum freezing and thawing rates.

A related object of the present invention is to provide a multichamber storage apparatus which facilitates the placement into long-term storage and the removal from long-term storage of multiple specimens having different optimum thawing and freezing protocols.

Another, more particular, object of the present invention is to provide such a multichamber storage apparatus which is easily adaptable to storing large numbers of specimens.

Yet another object of the present invention is to provide a method and apparatus for facilitating the thawing and/or freezing of biological specimens.

A more particular object of the present invention is to provide such a method and apparatus for facilitating thawing and/or freezing of a plurality of biological specimens having different optimal thawing and freezing rates and times.

SUMMARY OF THE INVENTION

A storage apparatus comprises, in accordance with the present invention, a housing for defining a plurality of chambers disposed one next to the other, the housing including partitions for separating the chambers from one another. Temperature controls for controlling temperature independently in each of the chambers is operatively connected to each of the chambers. Each one of the chambers has access to at least one other chamber contiguous with the one chamber. Supports are provided for holding a plurality of specimens within each chamber. A conveyor or transfer mechanism is provided for transfering selected specimens between contiguous chambers, independently of other specimens in the housing. In addition, access is provided to the housing to enable deposition and removal of given specimens from the housing.

Pursuant to another feature of the present invention, a control unit is operatively connected to the conveyor or trasnfer mechanism for activating that mechanism to transfer the selected specimens between the contiguous chambers. Preferably, the control unit includes means for tracking locations of specimens in the housing.

In addition, the control unit may include a timer for triggering transfer of the selected specimens by the conveyor or transfer mechanism at times in accordance with respective preestablished freezing and/or thawing protocols for the selected specimens. To that end, the control unit is preprogrammed with a plurality of freezing and thawing protocols in encoded form and includes means for automatically selecting from among the freezing and thawing protocols in accordance with specimen type.

Pursuant to another feature of the present invention, a selection device such as a keyboard is operatively connected to the control unit for inputting data into the control unit identifying the selected specimens.

Pursuant to a further feature of the present invention, the conveyor or transfer mechanism includes a revolving door in a partition between contiguous chambers. Alternatively, the conveyor or transfer mechanism includes a rail. More specifically, the rail may be a monorail, the selected specimens being temporarily mounted to the rail, for example, by hooks, to enable trasnfer of the specimens from one chamber to the next. The conveyor or transfer mechanism may alternatively take other equivalent forms, such as endless chains pr pulleys, moving sidewalk type mechanisms, and numerically controlled robotic handling devices.

Pursuant to a more specific embodiment of the present invention, one of the chambers constitutes a storage chamber for maintaining a plurality of biological specimens within a predetermined low temperature range, e.g., a cryogenic temperature range. Such a chamber advantageously operates as a longterm storage unit for maintaining specimens at cryogenic temperatures for indeterminate periods. The apparatus may comprise, in addition to the plurality of individually temperature-controlled chambers, a plurality of freezing chambers. Cooling devices are coupled to the freezing chambers for implementing a temperature change in each of the freezing chambers independently of temperature changes in all the other freezing chambers. A servomechanism is provided for retrieving a predetermined specimen from a respective selected freezing chamber and transfering the retrieved specimen to the long-term storage chamber. A control unit is operatively connected to the cooling devices and the servomechanism for operating the cooling devices to control a rate of temperature change in the selected freezing chamber and for activating the servomechanism to transfer the predetermined specimen from the selected freezing chambers to the long-term storage chamber.

Pursuant to another feature of the present invention, the control unit includes a timer for triggering retrieval of the predetermined specimen from the selected freezing chamber at a time in accordance with a respective pre-established freezing protocol for the predetermined specimen. The control unit is advantageously preprogrammed with a plurality of freezing protocols in encoded form and includes means for automatically selecting from among the freezing protocols in accordance with specimen type.

Pursuant to another specific embodiment of the present invention, wherein one of the chambers constitutes a long-term indefinite-period storage chamber, a plurality of thawing chambers are provided, together with heating devices for implementing a temperature change in each of the thawing chambers independently of temperature changes in each other of the thawing chambers. Another servomechanism is provided for retrieving a predetermined specimen from the long-term storage chamber and transfering the retrieved specimen to a selected one of the thawing chambers. A control unit is operatively connected to the heating devices and the servomechanism for operating the heating devices to control a rate of temperature change in the selected thawing chambers and for activating the servomechanism to transfer the predetermined specimen from the long-term storage chamber to the selected thawing chambers.

Pursuant to another feature of the present invention, the control unit includes a timer for triggering retrieval of the predetermined specimen from the selected thawing chamber at a time in accordance with a respective pre-established thawing protocol for the predetermined specimen. The control unit is advantageously preprogrammed with a plurality of thawing protocols in encoded form and includes means for automatically selecting from among the thawing protocols in accordance with specimen type.

A method for storing a perishable specimen comprises, in accordance with the present invention, the steps of: (a) inserting the specimen in a first chamber having a first temperature, (b) maintaining the specimen for at least a first predetermined period in the first chamber, (c) automatically moving the specimen, upon termination of the first predetermined period from the first chamber to a second chamber having a second temperature, and (d) maintaining the specimen for an indeterminate period in the second chamber. Upon termination of the indeterminate period, the specimen is automatically moved from the second chamber back to the first chamber. Upon shifting of the specimen from the second chamber to the first chamber, the specimen is maintained for at least a second predetermined period in the first chamber. In a final step, the specimen is removed from the first chamber upon termination of the second predetermined period.

Pursuant to another feature of the present invention, the first temperature is lower than room temperature and the second temperature is lower than the first temperature.

Pursuant to an additional feature of the present invention, the first predetermined period is at least partially automatically determined in accordance with a pre-established freezing protocol for the specimen.

Pursuant to yet another feature of the present invention, the pre-established freezing protocol is at least partially automatically selected from a plurality of freezing protocols stored in encoded form in a computer memory, the step of automatically selecting from among the freezing protocols being implemented in accordance with specimen type.

According to a supplemental feature of the present invention, the second predetermined period is at least partially automatically determined in accordance with a pre-established thawing protocol for the specimen.

According to yet a further feature of the present invention, the pre-established thawing protocol is at least partially automatically selected from a plurality of thawing protocols stored in encoded form in a computer memory, the step of automatically selecting from among the thawing protocols being implemented in accordance with specimen type.

BRIEF DESCRIPTION OF THE DRAWING

FIG. 10 is a perspective view of a transfer mechanism illustrated in FIG. 9.

FIG. 11 is a diagram of an alternative transfer mechanism.

FIG. 12 is a side elevational view of a portion of the transfer mechanism of FIG. 11.

FIG. 13 is a cross-ectional view taken along line XIII—XIII in FIG. 12.

DETAILED DESCRIPTION

Figure 1:
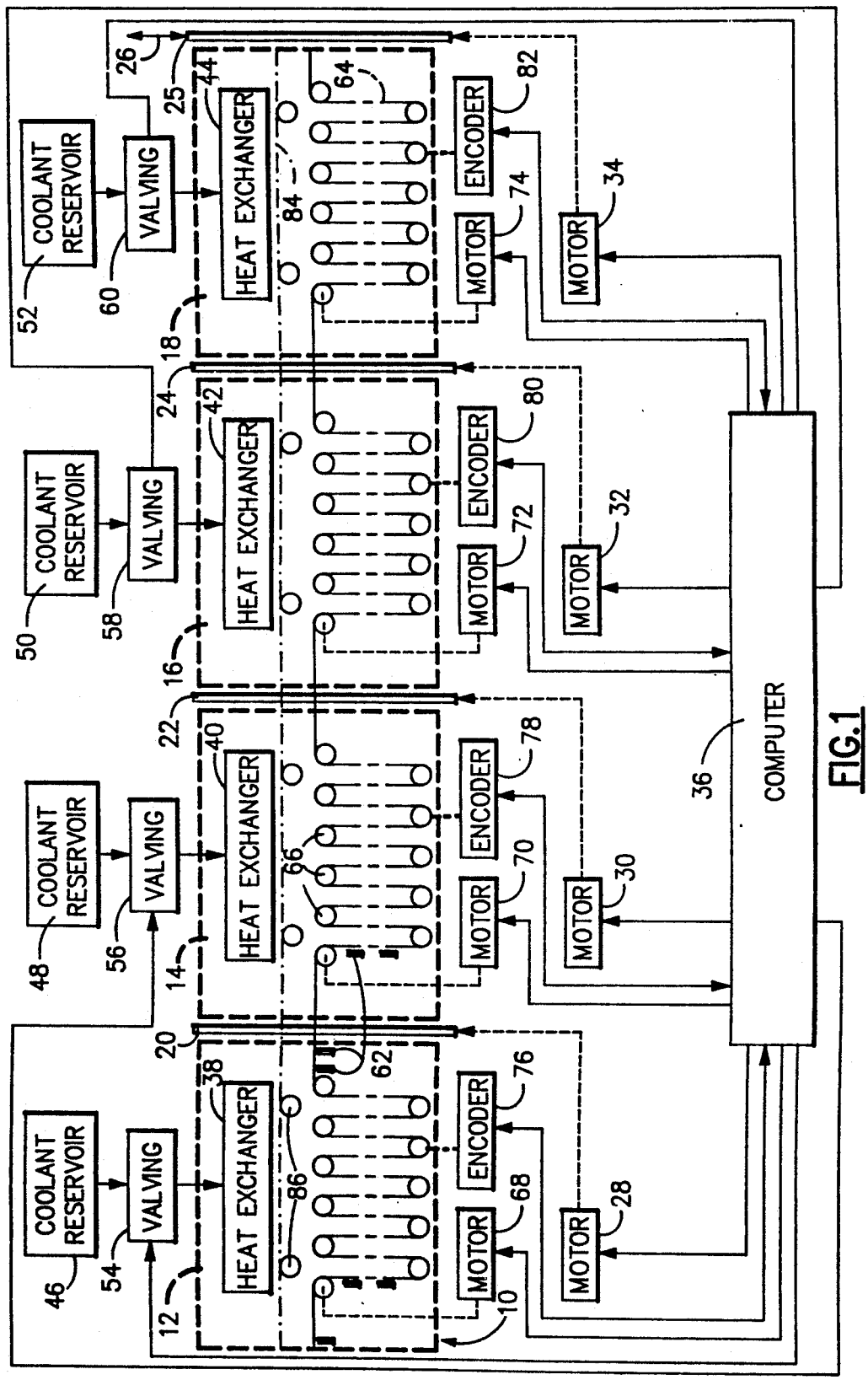
FIG. 1 is block diagram, with schematic representations, of a multichamber storage apparatus.

As illustrated in FIG. 1, a multichamber storage apparatus comprises a housing 10 defining a plurality of chambers 12, 14, 16 and 18 disposed one adjacent to the other. Chambers 12, 14, 16, and 18 represent a portion of a larger number of chambers arranged preferably in an endless array. However, the chambers of the multichamber storage apparatus may also be arranged in a linear array, as described hereinafter with reference to FIGS. 2 and 3.

Housing 10 includes a plurality of partitions 20, 22, 24 and 25 which separate chambers 12, 14, 16, and 18 from one another. Partitions 20, 22, 24 and 25 take the form of movable door members which are shiftable in the direction of arrow 26 by respective motor drives 28, 30, 32 and 34 acting under the control of a computer 36.

Each chamber 12, 14, 16, and 18 is provided with a respective heat exchanger unit 38, 40, 42 and 44 which communicates with a respective coolant reservoir 46, 48, 50 and 52 through a respective valve device 54, 56, 58 and 60 which is operated by computer 36. Heat exchanger units 38, 40, 42 and 44 may take any form suitable for providing the respective chamber 12, 14, 16, and 18 with a predetermined temperature. Concomitantly, the coolants contained in reservoirs 46, 48, 50 and 52 and circulated to heat exchanger units 38, 40, 42 and 44 under the control of computer 36 are different compositions having different cooling temperatures. For example, chamber 14 may be cooled by liquid nitrogen, while chambers 12 and 16 are cooled by a chlorofluorocarbon of one composition and chamber 18 by a chlorofluorocarbon of another, different composition having a boiling point different from the boiling point of the first chlorofluorocarbon composition. In that case, the boiling point of the chlorofluorocarbon coolant in reservoirs 46 and 50 is preferably lower than the boiling point of the coolant in reservoir 52.

Operating valve devices 54, 56, 58 and 60, computer 36 controls the temperatures of chambers 12, 14, 16, and 18. The temperature in each chamber is independent of the temperatures in the other chambers and is determined to a large extent by the boiling point of the respective coolant. The exact temperature may be varied through the action of computer 36 in response to non-illustrated temperature sensors located, for example, in each chamber 12, 14, 16, and 18.

As shown in FIG. 1, a multiplicity of specimen-containing receptacles 62 are supported on a pair of endless chains 64 (visible as only one chain in dot-dash line in the drawing) extending from one chamber 12, 14, 16, and 18 to the next. Chains 64 are in turn supported by a plurality of pulleys 66 to define in each chamber 12, 14, 16, and 18 a snaking path having a plurality of vertically oriented folds. A plurality of drive motors 68, 70, 72, and 74 are connected to respective driven pulleys for moving the chains and their receptacle payload along the snaking paths and from chamber to chamber.

Chains 64 and the details of the structure (e.g., bars) by which receptacles 62 are supported from chains 64 are described in commonly owned U.S. Pat. No. 4,969,336, the disclosure of which is hereby incorporated by reference. That prior application also discloses a mechanism for inserting and removing receptacles 62 individually from a cryogenic storage chamber. The same mechanism is used in the apparatus of FIG. 1. Preferably, the receptacle insertion and removal mechanism is placed at one chamber 12, 14, 16, or 18 only, most preferably a chamber having a highest temperature. However, in some applications it may be advantageous to insert and retrieve receptacles 62 from a plurality of chambers among chambers 12, 14, 16, and 18, for example, to facilitate and accelerate the insertion and retrieval process.

As described in U.S. Pat. No. 4,969,336, computer 36 tracks the locations of receptacles 62 during their travels through housing 10 via signals received from one or more encoders 76, 78, 80 and 82 operatively linked to pulleys 66 for monitoring the motion of chains 64. Computer 36 is also connected to drive motors 68, 70, 72 and 74 and to the insertion and retrieval mechanism(s) for controlling the operations thereof. As disclosed in U.S. Pat. No. 4,969,336, a keyboard or other input device (not illustrated herein) may be connected to computer 36 for instructing the computer to remove a certain receptacle from the multichamber storage apparatus. The computer determines the location of the requested receptacle from its memory whose contents are continuously updated by input from encoders 76, 78, 80 and 82.

As indicated diagrammatically in FIG. 1 by a dot-dash line 84 and pulley-representing circles 86, the path along which receptacles 62 are moved through housing 10 is an endless path. The receptacles may return to a starting position via a return path 84 which passes through the same chambers 12, 14, 16, and 18 (see FIGS. 2 and 3) or through different chambers (see FIGS. 4 and 5).

Upon shifting under the action of motor drives 28, 30, 32 and 34, partitions or door members 20, 22, 24 and 25 define access openings for enabling communication between each chamber 12, 14, 16, and 18 and at least one other chamber contiguous therewith. Partitions or door members 20, 22, 24 and 25 move swiftly and open no further and no longer than necessary to allow the passage of a bar (see U.S. Pat. No. 4,969,336) or bank of receptacles 62 from one chamber 12, 14, 16, or 18 to the next.

Figure 2:
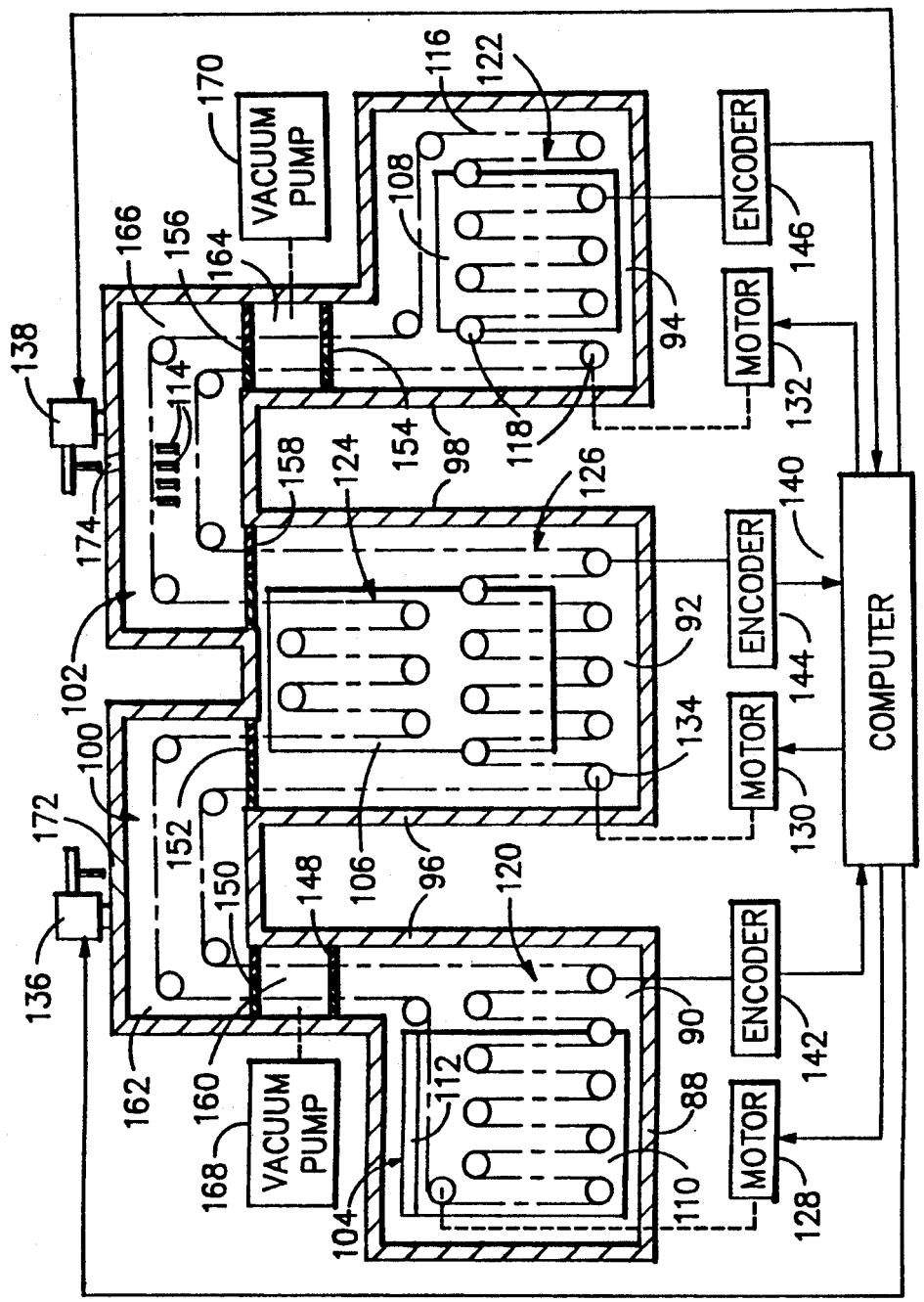
FIG. 2 is partially a block diagram and partially a schematic cross-sectional view of another multichamber storage apparatus.

As depicted in FIG. 2, another multichamber storage apparatus comprises a housing 88 defining three separate storage chambers 90, 92 and 94 disposed in a linear array in juxtaposition with each other. Housing 88 includes a plurality of partition elements 96 and 98 separating chambers 90, 92 and 94 from each other and defining in part a plurality of openings or passageways 100 and 102 extending from one chamber to the next.

Each chamber 90, 92 and 94 is provided with a respective heat exchanger unit 104, 106 and 108. At least one unit, for example, heat exchanger unit 104, takes the form of an L-shaped coolant container with a vertically oriented leg 110 and a horizontally oriented leg 112 having an open upper face, as described in detail in U.S. Pat. No. 4,969,336. Preferably, L-shaped coolant container 104 holds liquid nitrogen which sublimates off in a vaporous form to fill chamber 90, while heat exchanger units 106 and 108 contain liquid coolants such as chlorofluorocarbons which have higher boiling points than that of liquid nitrogen.

A multiplicity of specimen-containing receptacles 114 are supported on a pair of endless chains 116 (visible as only one chain in dot-dash line in the drawing) extending from chamber 90 to chamber 94 through chamber 92 and back again. Chains 116 are partially wound about a plurality of pulleys 118 to define a snaking path having one group of vertically oriented folds 120 and 122 in each chamber 90 and 94 and two groups of vertically oriented folds 124 and 126 in chamber 92. A plurality of drive motors 128, 130 and 132 are connected to respective driven pulleys 134 for moving chains 116 and their receptacle payload along the snaking path and from chamber to chamber.

The multichamber storage apparatus of FIG. 2 is provided with a pair of receptacle insertion and retrieval mechanisms 136 and 138 such as that described in detail in U.S. Pat. No. 4,969,336. Insertion and retrieval mechanisms 136 and 138 are mounted on portions of housing 88 above passageways 100 and 102.

Chains 116 and the details of the structure (e.g., bars) by which receptacles 114 are supported from chains 116 are also described in U.S. Pat. No. 4,969,336.

A computer 140 tracks the locations of receptacles 114 during their motion through housing 88 via signals received from one or more encoders 142, 144 and 146 operatively linked to pulleys 118 for monitoring the motion of chains 116. Computer 140 is also connected to drive motors 128, 130 and 132 and to insertion and retrieval mechanisms 136 and 138 for controlling the operations thereof. As set forth in U.S. Pat. No. 4,969,336, a keyboard or other input device (not illustrated herein) may be connected to computer for instructing the computer to remove a certain receptacle from the multichamber storage apparatus. The computer determines the location of the requested receptacle from its memory whose contents are continuously updated by input from encoders 142, 144 and 146.

As shown in FIG. 2, chambers 90 and 92 are separated from one another by sealing members 148, 150, and 152, and chambers 92 and 94 are separated from one another by sealing members 154, 156, and 158. Sealing members 148, 150 and 152 divide passageway 100 into a pair of buffer spaces 160 and 162, while sealing members 154, 156, and 158 divide passageway 102 into two intermediate spaces 164 and 166. Spaces 160 and 164 are connected to respective vacuum pumps 168 and 170 for evacuating those spaces of coolant which has penetrated from chambers 90 and 92. Spaces 162 and 166 are accessible by insertion and retrieval mechanisms 136 and 138 through slidable doors 172 and 174 (see Patent No. 4,969,336).

Sealing members 148, 150, 152 and 154, 156, 158 take the form of a multiplicity of parallel resilient fingers formed by cutting along parallel lines in a strip of flexible elastic material such as synthetic rubber. The fingers allow the traversal of the sealing members continuously by chains 116 and periodically by receptacles 114 and the support bars (see U.S. Pat. No. 4,969,336) thereof.

Cooling vapors or gases which have penetrated into spaces 160 and 164 and which are evacuated from those spaces by vacuum pumps 168 and 170 are replaced in chambers 90, 92 and 94 by sublimating vapors from heat exchanger units 104, 106 and 108. Alternatively, heat exchanger units 106 and 108, represent closed systems wherein the operative coolant material is not permitted to escape into chambers 92 and 94. In that case, vacuum pumps 168 and 170 are dispensed with and chambers 92 and 94 are filled with a gas such as nitrogen which is cooled by the respective heat exchanger units 106 and 108 to respective temperature levels higher than nitrogen's boiling point. Sealing members 148, 150, 152 and 154, 156, 158 then serve to prevent or at least inhibit the mixing of the nitrogen gas at the different temperatures.

Figure 3:
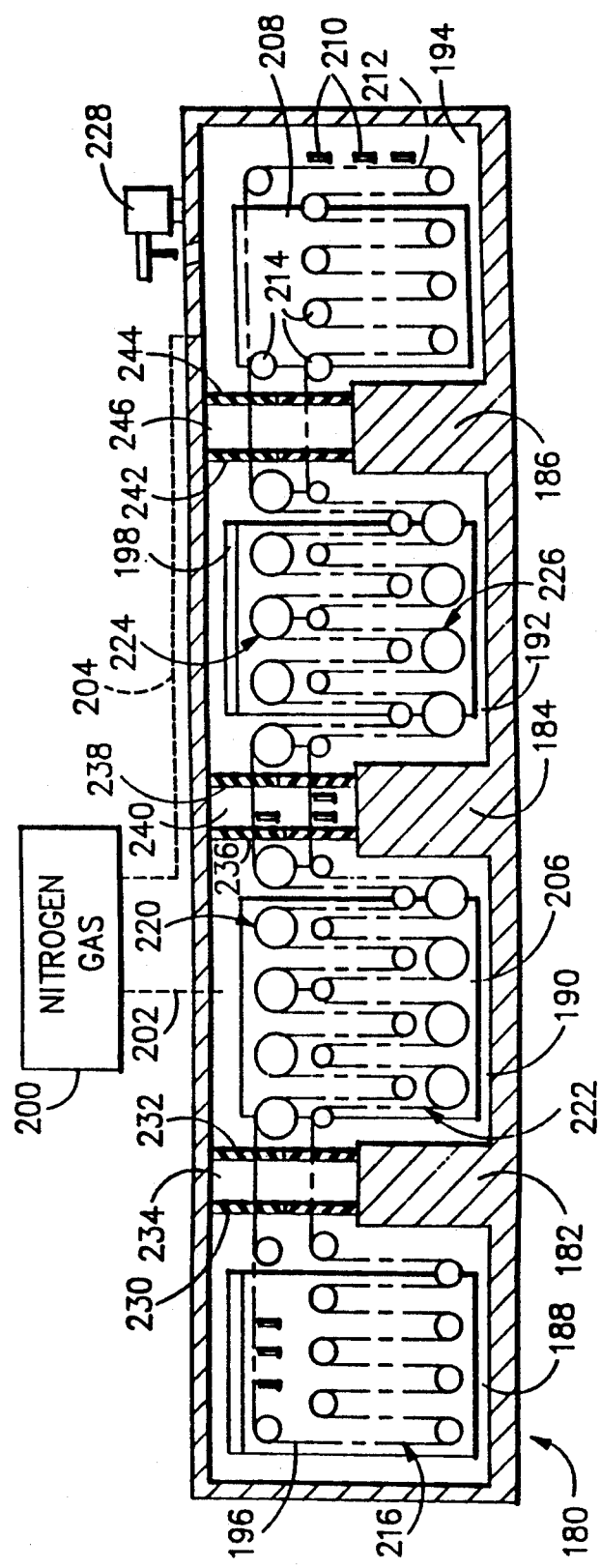
FIG. 3 is a partially cross-sectional view of another multichamber storage apparatus.

As illustrated in FIG. 3, another multichamber storage apparatus comprises a housing 180 and partition members 182, 184 and 186 which define a plurality of storage chambers 188, 190, 192 and 194. Storage chambers 188, 190, 192 and 194 are filled with gaseous nitrogen. In chambers 188 and 190, the nitrogen vapor is generated by a pool of liquid nitrogen stored in a respective L-shaped coolant reservoir or tank 196 and 198 having an open upper face, as described in U.S. Pat. No. 4,969,336. In chambers 190 and 194, gaseous nitrogen is supplied from an external storage tank 200 and fed to chambers 190 and 194 via conduits 202 and 204. In chambers 190 and 194, the gaseous nitrogen is cooled to temperatures exceeding the boiling point of liquid nitrogen by respective closed-loop heat exchanger units 206 and 208 containing a coolant such as a chlorofluorocarbon. Chambers 190 an 194 may be cooled to approximately the same temperature, the coolant in heat exchanger units 206 and 208 being the same composition. It is to be understood that several higher temperature storage chambers may be disposed between chambers 188 and 192.

A multiplicity of specimen-containing receptacles 210 are supported on a pair of endless chains 212 (visible as only one chain in dot-dash line in the drawing) extending from chamber 188 to chamber 194 through chambers 190 and 19 and back again. Chains 212 are partially wound about a plurality of pulleys 214 to define a snaking path having one group of vertically oriented folds 216 and 218 in each chamber 188 and 194 and two groups of vertically oriented folds 220, 222 and 224, 226 in each chamber 190 and 192. A plurality of drive motors (not shown) are connected to respective driven pulleys (not designated) for moving chains 21 and their receptacle payload along the snaking path and from chamber to chamber.

The multichamber storage apparatus of FIG. 3 is provided with at least one receptacle insertion and retrieval mechanism 228 such as that described in detail in U.S. Pat. No. 4,969,336. Insertion and retrieval mechanism 228 is mounted on housing 88 above chamber 194. Chains 212 and the details of the structure (e.g., bars) by which receptacles 210 are supported from chains 212 are also described in U.S. Pat. No. 4,969,336.

As shown in FIG. 3, chambers 188 and 190 are separated from one another by sealing members 230 and 232 which are distanced from one another to form a buffer space 234. Similarly, chambers 190 and 192 are spearated from one another by a pair of sealing members 236 and 238 which define an interchamber buffer space 240, while chambers 199 and 194 are divided from one anothe by two sealing members 242 and 244 which define a sealing space 250.

Sealing members 230, 232, 236, 238, 242 and 246 each take the form of a pair of strips of resilient flexible material such as rubber cut along multiplicity of parallel lines to form a multiplicity of resilient fingers. The fingers allow the traversal of the sealing members continuously by chains 212 and periodically by receptacles 210 and the support bars (see U.S. Pat. No. 4,969,336) thereof.

Computer control of the movement of chains 212 and the operation of insertion and retrieval mechanism 228 is implemented as described above with reference to FIGS. 1 and 2.

Figure 4:
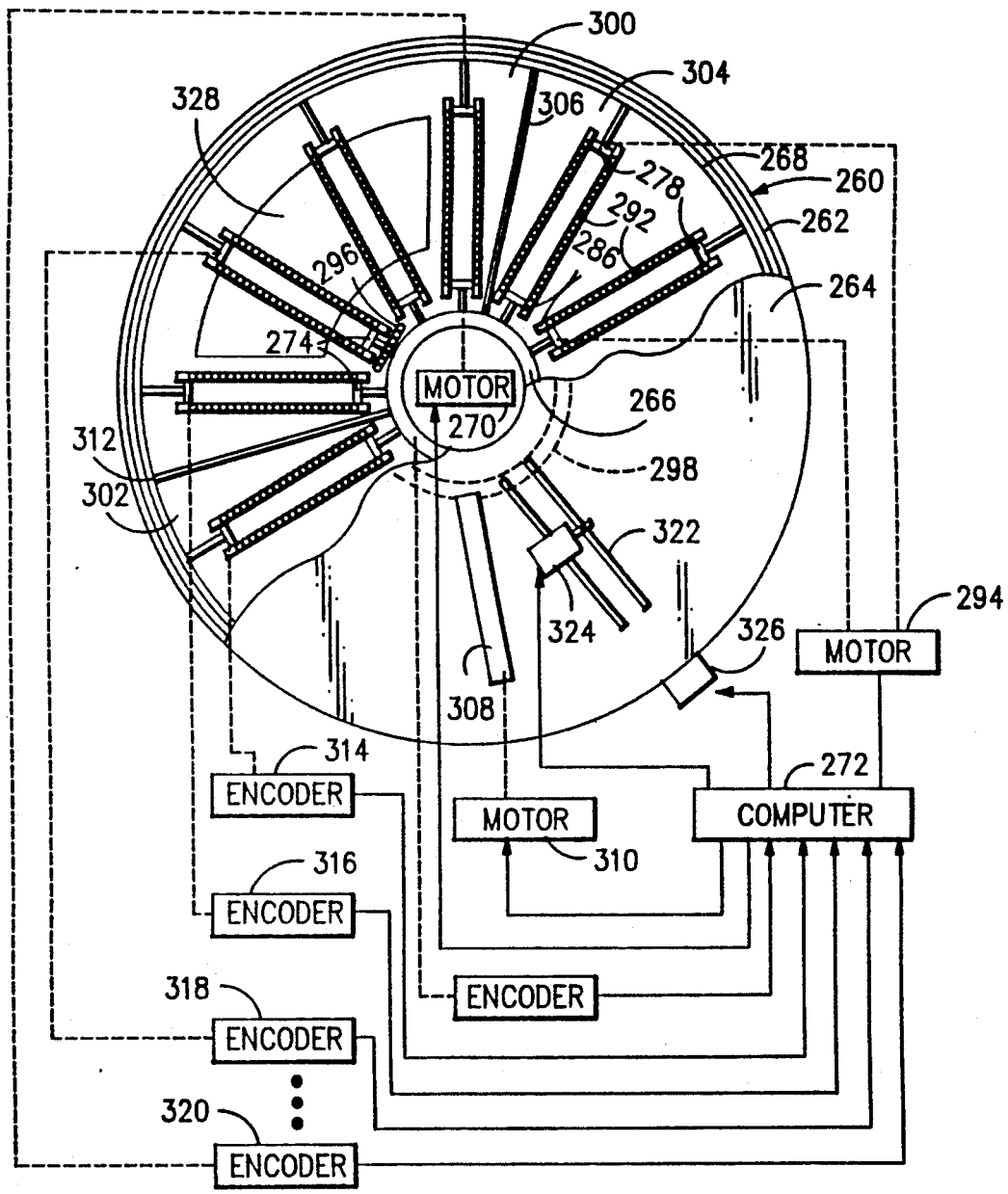
FIG. 4 is partially a block diagram, partially a schematic cross-sectional view and partially a top view of yet another multichamber storage apparatus.

As illustrated in FIG. 4, another multichamber storage apparatus comprises a housing 260 including a cylindrical outer wall 262 and a disk shaped upper wall 264. Disposed inside housing 260, coaxial with cylindrical outer wall 262 thereof is a an inner cylindrical drive member 266 and an outer cylindrical drive member 268. Drive members 266 and 268 are rotated about their axis of symmetry at a substantially constant velocity by a drive motor 270 which may be alternately energized and de-energized b a computer 272.

Figures 5, 6:
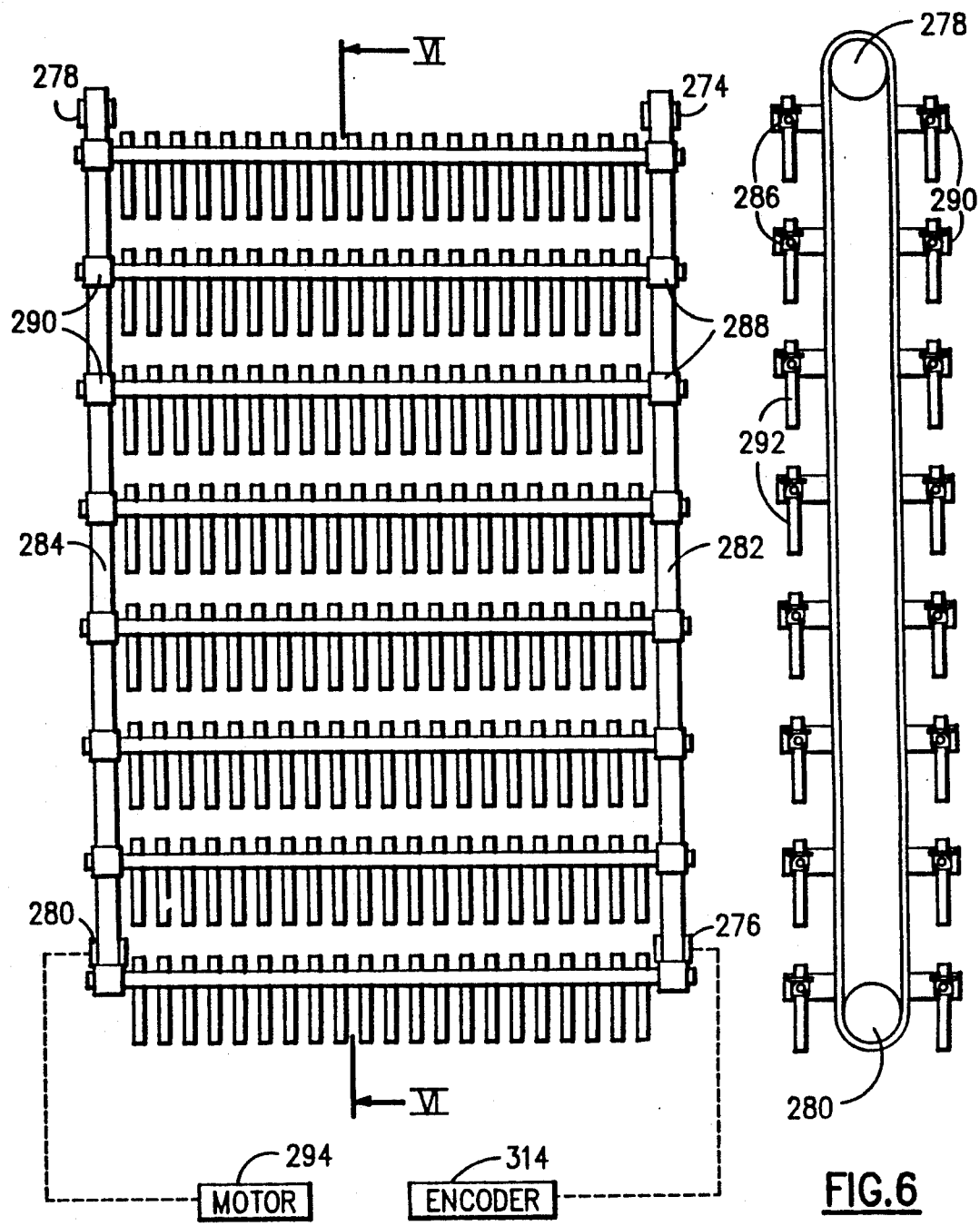
FIG. 5 is a schematic front elevational view of a bank of specimen-containing receptacles and support elements in the multichamber storage apparatus of FIGS. 4 and 5.
FIG. 6 is a schematic side elevational view of the specimen-containing receptacles and support elements of FIG. 6.

As shown in FIGS. 4, 5 and 6, inner drive member 266 carries a plurality of circumferentially spaced upper drive pulleys 274 and a plurality of circumferentially spaced lower drive pulleys 276, pulleys 274 and 276 being disposed in circular arrays longitudinally spaced from one another. Similarly, outer drive member 268 carries a plurality of circumferentially spaced upper drive pulleys 278 and a plurality of circumferentially spaced lower drive pulleys 280 disposed in two circular arrays longitudinally spaced from one another. Each pulley 274, 276, 278 and 280 is mounted to drive member 266 or 268 for rotation about an axis oriented radially with respect to housing wall 262, inner drive member 266 and outer drive member 268.

Each lower inner pulley 276 is drivingly coupled to a respective upper inner pulley 274 via a respective endless belt or chain 282 (FIG. 5), while each lower outer pulley 280 is drivingly linked to a respective upper outer pulley 278 via another endless belt or chain 284. Each inner belt or chain 282 and an associated outer belt or chain 284 carries a plurality of bars 286 each pivotably attached to the inner belt 282 via a first bracket 288 and pivotably secured to the outer belt 28 via a second bracket 290. Each bar 286 is provided with a row of equispaced openings (not shown) for receiving a plurality of specimen-containing receptacles or vials 292.

As indicated schematically in FIG. 4, at least one of each set of four pulleys 274, 276, 278 and 280 coupled to one another by belts 282 and 284 and bars 286 is driven in a rotary mode by a motor 294 operated under the control of computer or microprocessor 272. In an alternative or complementary drive system, each gang of coupled pulleys 274, 276, 278 and 280 is provided with a toothed drive gear 296 which meshingly engages a toothed ring 298 fastened to an inner surface of disk 264.

Motor 294 or gear 296 and ring 298 cause bars 286 and receptacles 292 to be moved up and down in a longitudinal direction, while motor 270 drives the specimen-containing receptacles and their supporting bars along a circular path through housing 260. The resulting motion is along a zig-zag or spiraling path. That path extends through a plurality of cooling chambers 300, 302 and 304 separated from one another by a plurality of door members 306 each in the form of a flexible web or sheet mounted to a respective coil housing 308 in turn disposed atop disk 264. Door members 306 are alternately opened and closed by respective motors 310 (only one shown) under the control of computer 272. Door members 306 have vertially extending edges 312 which deformably and slidingly engage an inner surface of outer drive member 268 or an inner surface of housing wall 262.

As illustrated in FIG. 4, computer 272 receives digitized information from a plurality of encoders 314, 316, 318, 320 ... each operatively connected to a respective inner or outer belt 282 or 284 for enabling computer 272 to track the locations of receptacles 292 during their spiraling or zig-zag motion through housing 260.

Upon receiving an instruction from an operator to retrieve a certain receptacle 292, computer 272 operates motors 270 and 294 to move the receptacle into position below a radially extending door 322 in disk 264. Computer 272 then opens the door 322 and activates a receptacle insertion and retrieval mechanism 324 to remove the selected receptacle and deposit it in an enclosure 326, as described in U.S. Pat. No. 4,969,336.

Each chamber 300, 302 and 304 is provided with a respective cooling system or heat exchanger unit 328 (only one shown in the drawing). As described hereinabove with reference to FIGS. 1-3, each chamber 300, 302 and 304 is cooled to a respective low temperature by means of a chemically different coolant composition. One coolant may be liquid nitrogen while other coolants are chlorofluorocarbons.

Figure 7:
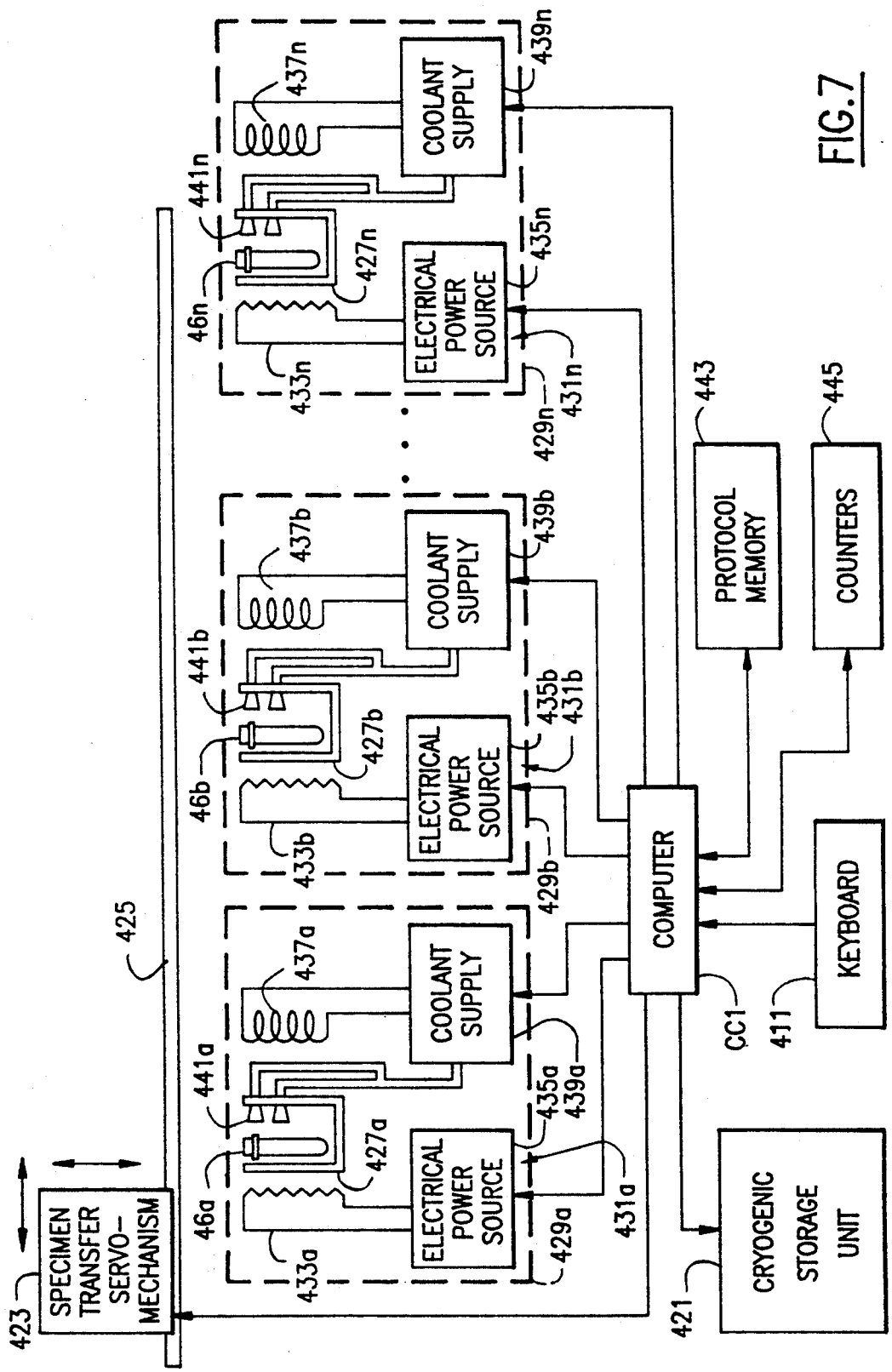
FIG. 7 is a diagram of a cryogenic storage system with automated thawing.

As illustrated in FIG. 7, a cryogenic storage system with automated thawing and freezing comprises a cryogenic storage unit 421 for storing a multiplicity of specimens for indeterminate periods. Preferably, storage unit 421 may take the form of a cyrogenic storage apparatus as described in U.S. Pat. No. 4,969,336 to Knippscheer et al. In that case, storage unit 421 incorporates a conveyor assembly for moving a plurality of specimen-containing ampules along a snaking path past an automatically actuated door. Storage unit 421 further incorporates encoders for enabling computer CCI to monitor or track the locations of the specimen-containing ampules within the storage unit. Storage unit 421 also includes a reservoir of liquid nitrogen or other cyrogenic substance and a servomechanism 423 (FIG. 7) for automatically inserting and retrieving individual specimens from the storage unit in response to signals from computer CC1. Servomechanism 423 may take the form of ampule insertion and extraction or retrieval mechanism 50 and rides along a rail 425 which extends from storage unit 421 past a plurality of thawing chambers 427a, 427b... 427n. Each thawing chamber 427a, 427b... 427n is part of a respective thawing unit 429a, 429b, ... 429n which includes a respective heat exchange assembly 431a, 431b, ... 431n for implementing a temperature ohange in each of the thawing chambers independently of temperature changes in the other chambers.

Each heat exchange assembly 431a, 431b, ... 431n in turn includes a resistive heating circuit 433a, 433b, ... 433n powered by a respective electrical source 435a, 435b, ... 435n. Electrical power sources 435a, 435b, ... 435n are controlled by computer CC1 to regulate the rates of warming of specimen-containing ampules 46a, 46b, ... 46n placed in the respective thawing chambers 427a, 427b... 427n. Alternatively or additionally, each thawing unit 429a, 429b, ... 429n includes a respective cooling circuit or coil 437a, 437b, ... 437n fed with coolant from a supply or reservoir 439a, 439b, ... 439n under the control of computer CC1. Coolant supplies 439a, 439b, ... 439n may also be connected to respective sets of spray nozzles 441a, 441b, ... 441n disposed in thawing chambers 427a, 427b, ... 427n for spraying a bath of liquid coolant such as liquid nitrogen or a chlorofluorocarbon mixture from the respective supply onto the ampule 46a, 46b, ... 46n being thawed.

The thawing of a specimen may be implemented, upon disposition of the specimen in an automatically preselected thawing chamber 427a, 427b, ... 427n, by gradually decreasing the flow of coolant through the respective coil 437a, 437b, ... 437n or through the respective nozzles 441a, 441b, ... 441n at a rate predetermined by computer CC1 in accordance with a warming or thawing protocol or schedule selected from a memory 443 in accordance with the type of specimen. Accordingly, blood is thawed at a rate different from a more solid biological tissue. Optimal thawing rates, including successive different rates for certain materials, are known in the art, as demonstrated by the disclosure of U.S. Pat. No. 4,712,607 to Lindemans et al., the disclosure of which is hereby incorporated by reference.

As an alternative to decreasing the rate of coolant flow to provide a warming effect, specimen-containing ampules 46a, 46b, ... 46n may be inserted into baths of coolant in the respective thawing chambers 427a, 427b, ... 427n. The respective heating circuits 433a, 433b, ... 433n are then energized at respective predetermined, possibly increasing, rates. Each such heating rate is predetermined by computer CCI in accordance with thawing schedules or protocols stored in encoded form in memory 443 for the different kinds of biological specimens.

It is to be noted that the function of specimen-transfer servomechanism 423 may be accomplished by a plurality of robot mechanisms which transfer specimen-containing ampules to one another and then deposit the ampules into thawing chambers 427a, 427b, ... 427n. It is to be noted further that thawing chambers may take any form known in the art. An appropriate form of thawing chamber is disclosed in U.S. Pat. No. 4,712,607. In accordance with that patent, power is supplied to a heat generating device whenever an actual, sensed, temperature falls below a desired temperature determined according to a temperature cycle stored in memory.

Thawing units 429a, 429b, ... 429n may be used for freezing specimens by reversing the functioning of certain components. For example, the flow of coolant through coolant coils 437a, 437b, ... 437n or through nozzles 441a, 441b, ... 441n may be increased at rates predetermined by computer CC1 in accordance with freezing protocols or schedules selected from memory 443 in accordance with the type of specimen. Thus, computer CCI may monitor and control freezing and thawing operations taking place simultaneously in different chambers 4227a, 427b, ... 427n.

As illustrated in FIG. 7, control unit or computer CC1 is connected to a bank of counters or timers 445 for triggering retrieval of the selected specimens from the storage unit at different times in accordance with respective pre-established thawing protocols for the selected specimens. Counters or timers 445 may form an area within the memory banks of computer CC1.

Computer CC1 is preprogrammed with specimen thawing protocols in encoded form, i.e., the thawing protocols are stored in memory 443. Computer CCI automatically selects from among the thawing protocols in accordance with specimen type. Typically, a selection made via a keyboard 411 will identify a particular specimen and a time that the specimen is to be available in a thawed state. In response to that input, computer CCl consults memory 443 (or an internal memory) and determines the type of biological material of the requested specimen. Computer CCl then accesses memory 443 to determine such parameters of the thawing protocol as the total time required for warming and the rates of warming for that type of specimen. Computer CCI then sets a timer in counter bank 445 to flag the time that the requested specimen is to be removed from storage unit 421.

Counters 445 thus alert computer CCl as to times for initiating thawing procedures on selected specimens. Counters 445 may also be set by computer CCl for flagging changes in warming rates, as well as for signaling the termination of thawing operations. Computer CCI may activate an optional signaling device (not illustrated) to alert human operators that thawing has been completed for one or more selected specimens.

Upon determining that the time has arrived for commencing a thawing operation on a requested specimen, computer CC1 transmits control signals to storage unit 421 and servomechanism 42 to induce those components to extract the selected specimen from the storage unit and to transfer the retrieved specimen to a thawing chamber 427a, 427b, ... or 427n selected by the computer. Computer CC1 selects the thawing chamber basically according to availability, but if the thawing chambers have different design specifications, for example, different thawing rate capabilities and capacities, then the selection can be implemented in accordance with more detailed information.

As discussed above, in order to control the warming of the retrieved specimen upon disposition thereof in the selected thawing chamber 427a, 427b, ... 427n, computer CC1 activates the respective electrical power source 435a, 435b, ... 435n and/or opens a valve in the respective coolant supply 439a, 439b, ... 439n to thereby control the rate at which heat is provided to the thawing chamber. As pointed out above, the control of the thawing process may be implemented pursuant to the teachings of U.S. Pat. No. 4,712,607.

It is to be noted that computer CC1 may be controlling thawing cycles for several specimens simultaneously to ensure that all such specimens attain a desired thawed state at approximately the same time. Computer CC1 takes into account the different thawing protocols This result is advantageous, for example, in having a plurality of specimens thawed over night and ready for experimental research at the beginning of the work day.

As noted hereinabove, the apparatus illustrated in FIG. 7 is also utilizable for controlling the simultaneous or sequential freezing of a plurality of biological specimens. Computer CC1 first selects a freezing chamber from among chambers 427a, 427b, ... 427n. The selection is made in accordance with the specimen type and other information entered into computer CC1 via keyboard 411. Sometimes the selection is arbitrary, depending only on availability of chambers 427a, 427b, ... 427n.

Upon the selection of a freezing chamber from among chambers 427a, 427b, ... 427n, computer CC1 activates servomechanism 423 to transfer the specimen to the selected chamber 427a, 427b, ... or 427n. The specimen to be frozen is placed, for example, by hand into enclosure 442 and is then transfered by servomechanism 423 from enclosure 442 to the proper chamber 427a, 427b, ... or 427n.

Prior to the commencement of freezing operations and preferably prior to placement of the specimen into the freezing chamber, computer CC1 accesses in memory 443 a table of freezing protocols, i.e., optimal freezing periods and associated freezing rates, for a multiplicity of specimen types. From that table, computer CCI determines the optimal freezing period and rate or rates for the specimen to be frozen. Thus, the timing of subperiods having different freezing rates is determined by computer CC1 in accordance with freezing rate information from member 443 and is implemented by the computer with the aid of counters 445.

Upon deposition of the specimen into the selected freezing chamber 427a, 427b, ... or 427n, computer CC1 activates the respective power source 431a, 431b, ... or 431n and/or the respective coolant supply 439a, 439b, ... or 439n to control the rate of freezing of the specimen. More particularly, the rate of freezing may be controlled by modifying the rate of coolant flow through the respective coil 437a, 437b, ... or 437n or out of the respective spray nozzle 441a, 441b, ... or 441n. The rate of cooling may be finely tuned through the use of resistive heating circuits 433a, 433b, ... 433n.

Upon termination of the cooling operation, as determined by computer CCI from the freezing protocol information for the subject specimen and through the use of counters 445, or, alternatively or additionally, as determined by computer CCl in response to temperature sensor data sensors (not shown), computer CCI activates servomechanism 423 to remove the frozen specimen from the freezing chamber 427a, 427b, ... or 427n and to transfer the frozen specimen to storage unit 421.

It is to be noted that the freezing chambers 427a, 427b, ... 427n may take any form known in the art. Such chambers are disclosed in U.S. Pat. No. 4,712,607 and U.S. Pat. No. 4,304,293 to Scheiwe et al., the disclosure of which is hereby incorporated by reference.

Figure 8:
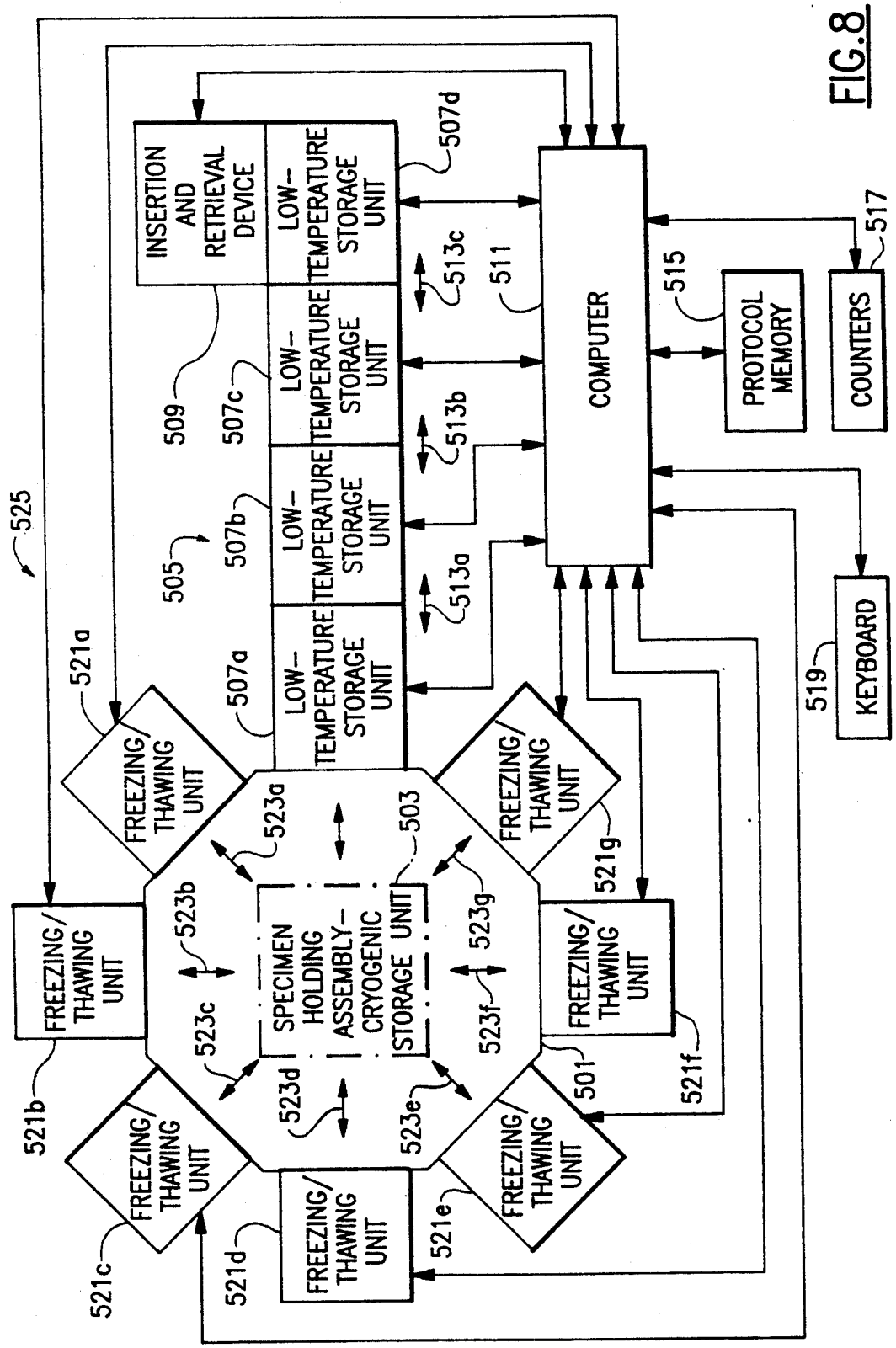
FIG. 8 is a block diagram of a multichamber storage apparatus in accordance with the present invention.

As illustrated in FIG. 8, a multiple chamber storage apparatus with controlled thawing and freezing comprises a main cryogenic storage unit 501 provided with an assembly 503 for holding biological or other specimens for long-term storage of indeterminate periods. Cryogenic unit 501 is coupled to a linear array 505 of interconnected storage units 507a, 507b, 507c and 507d. Generally, storage units 507a, 507b, 507c and 507d are used for short-term storage of specimens on their way to long term storage in cryogenic unit 501. However, it is also contemplated that some specimens not requiring cryogenic storage may be stored for indefinite periods in one or more storage units 507a, 507b, 507c and 507d.

Storage unit 507d is the farthest from cryogenic unit 501 and has the highest temperature, which is lower than room temperature. The other short-term storage units 507a, 507b and 507c define storage chambers maintained at respective predetermined temperatures between the cryogenic temperature of storage 501 unit and the temperature of terminal unit 507d. Preferably, the temperatures of short-term storage units 501, 507a, 507b, 507c and 507d increase in a monotonic sequence from the temperature of liquid nitrogen to a substantially warmer temperature below room temperature.

An insertion and retrieval device 509 is coupled to storage unit 507d for alternately depositing into that storage unit 507d and extracting therefrom individual specimens or groups of specimens. The operation of insertion and retrieval device 509 is controlled by a computer 511. Computer 511 is connected to low-temperature storage units 507a, 507b, 507c and 507d for monitoring and controlling the transfer of specimens between the storage units, as indicated schematically by arrows 513a, 513b, 513c, as well as for monitoring and controlling temperature and for tracking the locations of specimens which are in temporary or long-term storage inside units 507a, 507b, 507c and 507d.

In accordance with the kinds of specimens loaded into terminal storage unit 507d, and pursuant to freezing protocols stored in electrically encoded form in a computer memory 515, computer 511 controls the lengths of time that the loaded specimens are maintained in sequence in each of the successive storage units 507d, 507c, 507b and 507a prior to transfer to long-term cryogenic unit 501. In addition, control unit or computer 511 is connected to a bank of counters or timers 517 in part for keeping track of the intervals that the different specimens have been stored in the various storage units 507a, 507b, 507c and 507d. Counters or timers 517 may form an area within the memory banks of computer 511.

In the event that specimens to be retrieved from cryogenic unit 501 are to be thawed via passage through storage units 507a, 507b, 507c and 507d, computer 511 also controls the lengths of time that stored specimens are maintained in sequence in each of the successive storage units 507a, 507b, 507c and 507d after retrieval from cryogenic unit 501.

Cyrogenic storage unit 501 is alos connected to a plurality of freezing/thawing units 521a, 521b, 521c, 521d, 521e, 521f and 521g. Each freezing/thawing unit 521a, 521b, 521c, 521d, 521e, 521f and 521g incorporates a heat exchange assembly similar to heat exchange assemblies 431a, 431b, ... 431n of FIG. 7 for implementing a temperature change in each of the freezing/thawing units independently of temperature changes in the other units. Thus, each freezing/thawing unit includes a resistive heating circuit similar to resistive heating circuits 433a, 433b, ... 433n. Alternatively or additionally, each freezing/thawing unit 521a, 521b, 521c, 521d, 521e, 521f and 521g includes a respective cooling circuit or coil similar to cooling circuits 437a, 437b, ... 437n and/or respective sets of spray nozzles similar to spray nozzles 441a, 441b, ... 441n for spraying a bath of liquid coolant such as liquid nitrogen or a chlorofluorocarbon mixture from the respective supply onto a specimen or group of specimens (e.g., in a tray or rack).

Freezing/thawing units 521a, 521b, 521c, 521d, 521e, 521f and 521g also include transfer or conveyance mechanisms schematically indicated by arrows 523a, 523b, 523c, 523d, 523e, 523f and 523g for automatically moving frozen specimens into cryogenic storage unit or removing from that unit specimens to be thawed. The transfer or conveyance mechanisms (523a, 523b, 523c, 523d, 523e, 523f and 523g) may take the form of one or more robotic transfer devices and a revolving door or monorail mechanism, as described hereinafter with reference to FIGS. 9-13 and storage units 507a, 507b, 507c and 507d.

Computer 511 is operatively coupled to freezing/thawing units 521a, 521b, 521c, 521d, 521e, 521f and 521g for controlling freezing and/or thawing operations therein and for activating transfer and conveyance mechanisms (523a, 523b, 523c, 523d, 523e, 523f and 523g) to move specimens into and out of the freezing/thawing units.

The provision of both storage units 507a, 507b, 507c and 507d and freezing/thawing units 521a, 521b, 521c, 521d, 521e, 521f and 521g to cryogenic unit 501 enhances the options of computer 511 with respect to the specific paths for freezing and thawing selected specimens and specimen groups. More specifically, with respect to retrieval, when a specimen or group of similar specimens (all held, for example, in a common tray or rack) stored in long-term cryogenic unit 501 is needed, a selection made via a keyboard 519 will identify the specimen or group of specimens and a time that the specimen or specimens are to be available in a thawed state. In response to that input, computer 511 consults memory 515 (or an internal memory) and determines the type of biological material of the requested specimen. Computer 511 then accesses memory 515 to determine such parameters of the thawing protocol as the total time required for warming and the rates of warming for that type of specimen. In accordance with all this information, computer 511 determines the optimum route for thawing. More particularly, computer 511 determines whether storage units 507a, 507b, 507c and 507d or one or more freezing/thawing units 521a, 521b, 521c, 521d, 521e, 521f and 521g are to be used to thaw the selected specimens.

Upon determining the thawing route, computer 511 sets a timer in counter bank 517 to flag the time that the requested specimen or group of specimens is to be removed from storage unit 501. Upon termination of the set period, computer 511 initiates a thawing sequence.

Counters 517 thus alert computer 511 as to times for initiating thawing procedures on selected specimens. Counters 517 may also be set by computer 511 for flagging changes in warming and cooling rates, as well as for signaling the termination of thawing or freezing operations. Computer 511 may activate an optional signaling device (not illustrated) to alert human operators that thawing or freezing has been completed for one or more selected specimens.

Upon determining that the time has arrived for commencing a thawing operation on a requested specimen or group of specimens (which may be collected in a common tray or rack), computer 511 transmits control signals to storage unit 501 and particularly to a servomechanism therein to induce that component to extract the selected specimen or group of specimens from the specimen holding assembly 503 and to transfer the retrieved specimen(s) to a freezing/thawing unit 521a, 521b, ... or 521g selected by the computer. Computer 511 selects the freezing/thawing unit basically according to availability, but if the freezing/thawing units have different design specifications, for example, different thawing rate capabilities and capacities, then the selection can be implemented in accordance with more detailed information. In addition, some of the freezing/thawing units 521a, 521b, ... and 521g may be allocated solely to freezing operations, while others are reserved for thawing operations.

With respect to the deposition of a specimen or a group of specimens into the storage apparatus of FIG. 8, keyboard 519 is used to identify the type of cellular material comprising the specimen(s). Computer 511 then accesses protocol memory 515 to determine the optimum freezing path for the specimen(s), based on the protocol information. The computer thus identifies whether 507a, 507b, 507c and 507d, on the one hand, or a freezing/thawing unit 521a, 521b, 521c, 521d, 521e, 521f or 521g, on the other hand, is to be used for preparing the specimen(s) for long-term storage in cryogenic unit 501. Of course, as mentioned hereinabove, one alternative is to permanently store the specimen(s) in one of the higher-temperature storage units In determining the optimum freezing path, computer 501 also ascertains the optimum durations that the specimen(s) remains in each of the successive storage units 507d, 507c, 507b or 507a or the optimum cooling rates and durations in the selected freezing/thawing unit 521a, 521b, 521c, 521d, 521e, 521f or 521g.

The storage apparatus of FIG. 8 includes a housing 525 defined by the exterior walls of cryogenic unit 501, storage units 507a, 507b, 507c and 507d, and freezing/thawing units 521a, 521b, 521c, 521d, 521e, 521f and 521g. In use, computer 511 coordinates, monitors, tracks and controls the freezing, thawing and storage of numerous biological specimens having different freezing, thawing and storage requirements. Specimens or groups of specimens are moved between storage units 507a, 507b, 507c and 507d in both directions, at different rates, that is, with different stays in the different storage units 507a, 507b, 507c and 507d. In addition, specimens or groups of specimens are moved between cryogenic unit 501 and each freezing/thawing unit 521a, 521b, 521c, 521d, 521e, 521f and 521g independently of the specimens in storage units 507a, 507b, 507c and 507d and independently of the use of the other freezing/thawing units 521a, 521b, 521c, 521d, 521e, 521f and 521g.

Figure 9:
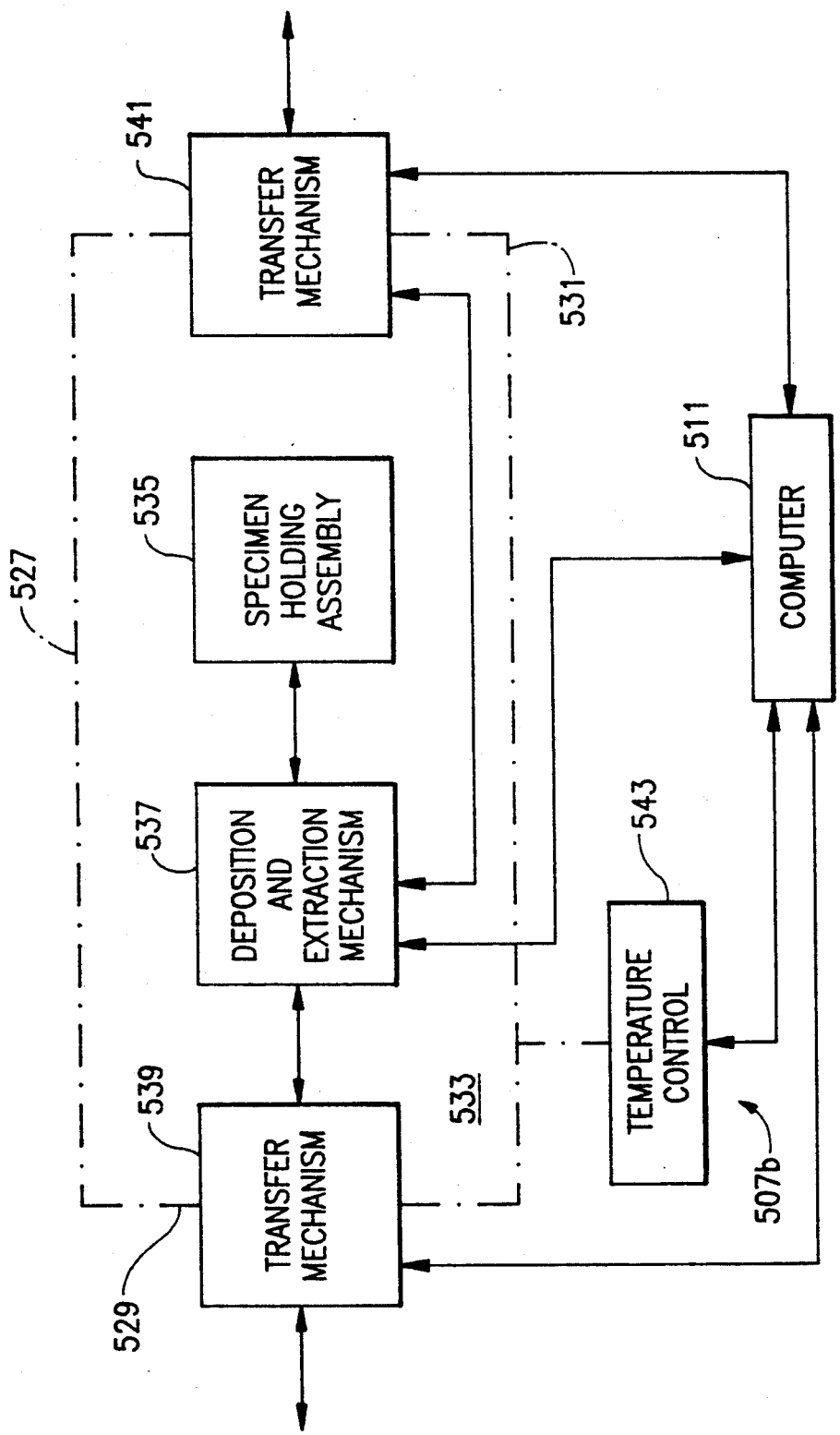
FIG. 9 is a block diagram of a low-temperature storage unit illustrated in FIG. 8.

As depicted in FIG. 9, storage unit 507b, which is essentially structurally identical to storage units 507a, 507c and 507d, comprises an external wall 527 and partitions 529 and 531 defining a chamber 533. Partitions 529 and 531 are party walls also serving to define the adjacent storage units 507a and 507c. Inside chamber 533 is a specimen holding assembly 535 which may take virtually any form. A deposition and extraction robot mechanism 537 accesses holding assembly 535 to deposit specimens therein and to remove speoimens therefrom. Deposition and extraction mechanism 537 cooperates with transfer mechanisms 539 and 541 to move specimens between storage unit 507b and adjacent units 507a and 507c. Transfer mechanisms 539 and 541 thus penetrate or bridge respective partitions 529 and 531 to enable the conveyance of specimens between adjacent storage chambers.

As further illustrated in FIG. 9, a temperature control assembly 543 is operatively connected to storage unit 507b for maintaining a predetermined temperature in chamber 533. Computer 511 is operatively linked to temperature control assembly 543, deposition and extraction robot mechanism 537 and transfer mechanisms 539 and 541 to monitor and control the operations thereof.

Transfer mechanisms 539 and 541 may take any form capable of transfering single or multiple specimens between adjacent storage units 507a, 507b, 507c and 507d and between cryogenic unit 501 and storage unit 507a. FIG. 10 illustrates a revolving door or drum transfer mechanism 545 including a partially hollow drum 547 rotatably mounted to a partition 529 or 531 for rotation about a vertical axis 549. Drum 547 is engaged by sealing strips 551 mounted to the partition 529 or 531 to insulate low-temperature storage chamber 533 from adjacent schambers (not shown).

As further illustrated in FIG. 10, drum 547 is provided with receptacles 553 and 555 for receiving a tray or rack and individual specimen-containing ampules, respectively. Clearly, drum 547 may be designed to handle specimens and specimen receptacles of widely varying shapes and sizes. In addition, drum 547 may be provided with a sliding door or cover plate 557 reciptratable as indicated by arrow 559 for closing the drum during rotation thereof about axis 549.

Robot mechanism 537 alternately deposits specimens or specimen containers into receptacles 553 and 555 and removes specimens or specimen containers from receptacles 553 and 555, depending on whether the specimens are being thawed or frozen. As described above, the times of specimen transfer are orchestrated by comptuer 511 in accordance with predetemined specimen freezing and thawing protocols.

Another type of transfer mechanism for conveying specimens or groups of specimens between adjacent storage units 507a, 507b, 507c and 507d is schematically indicated in FIG. 11. Storage unit 507b communicates with adjacent storage units 507a and 507c via a pair of endless rails 561 and 563 which traverse partitions 529 and 531, respectively. As shown in FIGS. 12 and 13, specimens may be temporarily fastened to rails 561 and 563 via hooks 565 mounted on carriers 567 movably mounted to the rails. The carriers 567 may be driven along rails 561 and 563, for example, via endless chains. Computer 511 monitors the locations of specimens along rails 561 and 563 via encoders (not illustrated), as described hereinabove with reference to FIGS. 1 and 2.

Transfer mechanisms 539 and 541 ma take other forms equivalent to those described hereinabove, such as conveyor belts or moving sidewalks. Alternatively, the function of transfer mechanisms 539 and 541 may be performed by robotic deposition and extraction mechanisms 537 of adjacent storage units 507a, 507b, 507c and 507d. In such a design, deposition and extraction mechanisms 537 pass specimens directly to one another through flexible seals in partitions 529 and 531.

Figure 14:
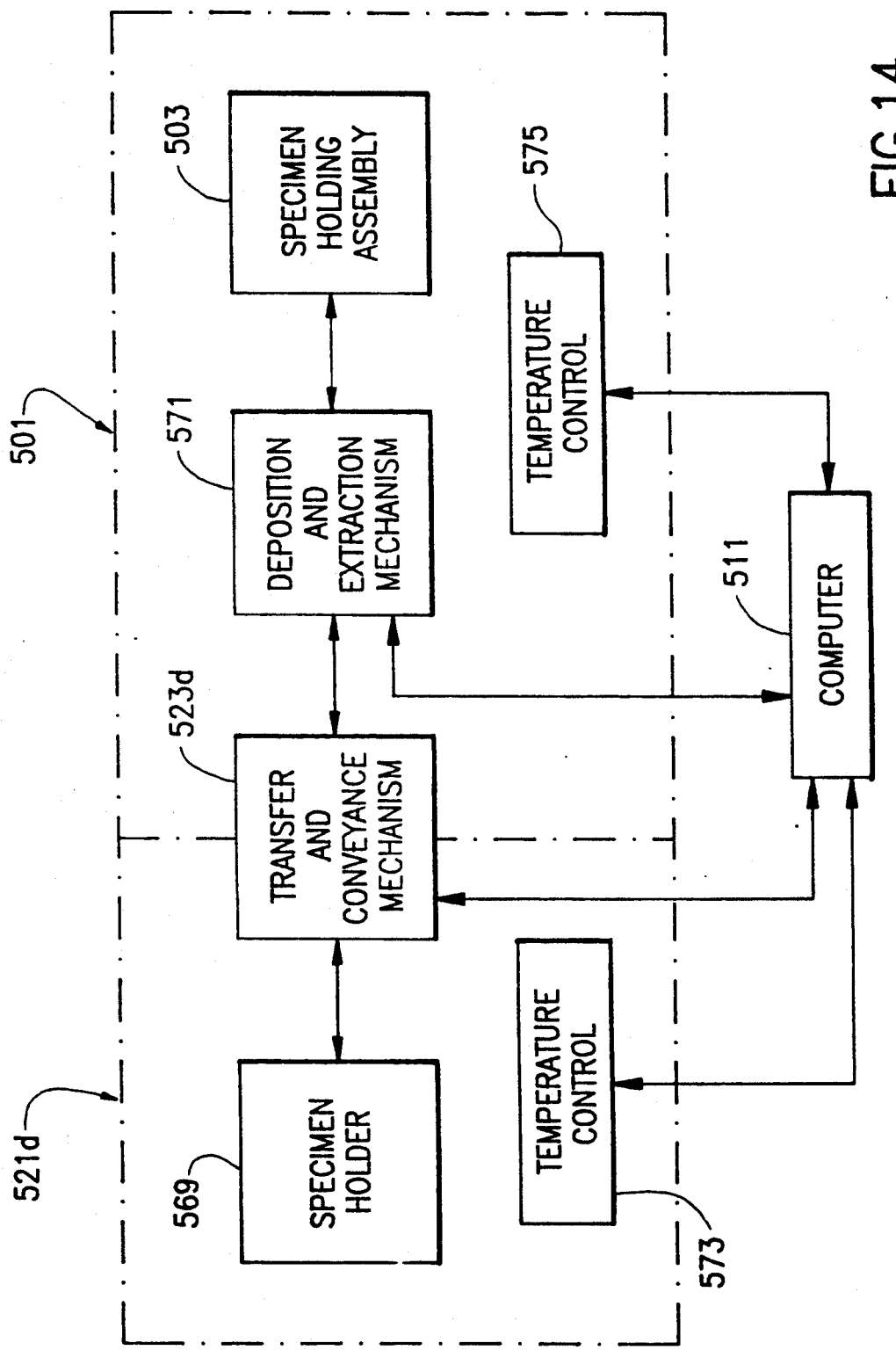
FIG. 14 is a block diagram of a freezing/thawing unit and a cryogenic storage unit illustrated in FIG. 8.

As shown in FIG. 14, representative freezing/thawing unit 521d incorporates a specimen holder 569 such as a rack or a tray. Specimens or groups of specimens are deposited into hodler 569 and alternately removed therefrom by a robotic transfer and conveyance mechanism 523d. That mechanism in turn cooperates with a robotic deposition and extraction mechanism 571 inside cryogenic unit 501 to shift selected specimens between specimen holding assembly 503 of the cryogenic unit and holder 569 of the freezing/thawing unit 521d. Units 521d and 501 include respective temperature control components 573 and 575. As stated above, temperature control component 573 of freezing/thawing unit 521d may take the form of heat exchange assemblies 431a, 431b, ... 431n of FIG. 7 for implementing a temperature change in each of the freezing/thawing units 521a, 521b, ... 521g independently of temperature changes in the other units. Temperature control component 575 of cryogenic unit 501 may include coolant containers and circulating circuits of conventional liquid nitrogen units. Alternatively, temperature control component 575 may take a form described hereinabove with reference to FIG. 2, namely, an L-shaped coolant container with a vertically oriented leg and a horizontally oriented leg having an open upper face, as described in detail in U.S. Pat. No. 4,969,336, incorporated by reference herein.

Computer 511 obtains temperature and encoder feedback from cryogenic unit 501, storage units 507a, 507b, 507c and 507d and freezing/thawing units 521a, 521b, 521c, 521d, 521e, 521f and 521g. Such feedback may include signals from scanners or readers (not illustrated) which verify the identities of specimens. For example, laser bar-code readers such as that described in U.S. Pat. No. 4,969,336 may provide confirmatory signals to computer 511 during insertion and retrieval, deposition and extraction, and transfer and conveyance operations. All of these features allow computer to minimize error in the automatic freezing, thawing and storage of thousands of specimens simultaneously.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A storage apparatus comprising:

housing means for defining a plurality of chambers disposed one next to the other, said housing means including partition means for separating said chambers from one another;

temperature control means for controlling temperature independently in each of said chambers;

first access means for enabling communication between each one of said chambers and at least one other of said chambers contiguous with said one of said chambers;

support means for holding a plurality of specimens within each of said chambers;

conveyance means for transfering selected specimens between contiguous ones of said chambers via said first access means, independently of other specimens in said housing means; and second access means for enabling deposition and removal of given specimens from said housing means.

2. The apparatus according to claim 1, further comprising control means operatively connected to said conveyance means for activating said conveyance means to transfer said selected specimens between said contiguous chambers.

3. The apparatus according to claim 2 wherein said control means includes means for tracking locations of specimens in said housing means.

4. The apparatus according to claim 2 wherein said control means includes timing means for triggering transfer of said selected specimens by said conveyance means at times in accordance with respective pre-established thawing protocols for said selected specimens.

5. The apparatus according to claim 4 wherein said control means is preprogrammed with a plurality of thawing protocols in encoded form and includes means for automatically selecting from among said thawing protocols in accordance with specimen type.

6. The apparatus according to claim 2 wherein said control means includes timing means for triggering transfer of said selected specimens by said conveyance means at times in accordance with respective pre-established freezing protocols for said selected specimens.

7. The apparatus according to claim 6 wherein said control means is preprogrammed with a plurality of freezing protocols in encoded form and includes means for automatically selecting from among said freezing protocols in accordance with specimen type.

8. The apparatus according to claim 2, further comprising selection means operatively connected to said control means for inputting data into said control means identifying said selected specimens.

9. The apparatus according to claim 1 wherein said second access means is disposed at one of said chambers having a highest temperature among said chambers.

10. The apparatus according to claim 1, further comprising closure means for providing a seal at said first access means to restrict movement of said coolants between said chambers.

11. The apparatus according to claim 10 wherein said closure means includes flexible sealing members disposed at locations between said chambers.

12. The apparatus according to claim 1 wherein said conveyance means includes a revolving door.

13. The apparatus according to claim 1 wherein said conveyance means includes a rail.

14. The apparatus according to claim 1 wherein one of said chambers constitutes storage means for maintaining a plurality of biological specimens within a predetermined low temperature range, further comprising:

a plurality of freezing chambers;

cooling means for implementing a temperature change in each of said freezing chambers independently of temperature changes in each other of said freezing chambers;

servomechanism means for retrieving a predetermined specimen from a respective selected one of said freezing chambers and transferring the retrieved specimen to said storage means; and control means operatively connected to said cooling means and said servomechanism means for operating said cooling means to control a rate of temperature change in said selected one of said freezing chambers and for activating said servomechanism means to transfer said predetermined specimen from said selected one of said freezing chambers to said storage means.

15. The apparatus defined in claim 14 wherein said control means includes timing means for triggering retrieval of said predetermined specimen from said selected one of said freezing chambers at a time in accordance with a respective preestablished freezing protocol for said predetermined specimen.

16. The apparatus defined in claim 15 wherein said control means is preprogrammed with a plurality of freezing protocols in encoded form and includes means for automatically selecting from among said freezing protocols in accordance with specimen type.

17. The apparatus according to claim 1 wherein one of said chambers constitutes storage means for maintaining a plurality of biological specimens within a predetermined low temperature range, further comprising:
a plurality of thawing chambers;
heating means for implementing a temperature change in each of said thawing chambers independently of temperature changes in each other of said thawing chambers;
servomechanism means for retrieving a predetermined specimen from said storage means and transfering the retrieved specimen to a selected one of said thawing chambers; and
control means operatively connected to said heating means and said servomechanism means for operating said heating means to control a rate of temperature change in said selected one of said thawing chambers and for activating said servomechanism means to transfer said predetermined specimen from said storage means to said selected one of said thawing chambers.

18. The apparatus defined in claim 17 wherein said control means includes timing means for triggering removal of said predetermined specimen from said selected one of said thawing chambers at a time in accordance with a respective preestablished thawing protocol for said predetermined specimen.

19. The apparatus defined in claim 18 wherein said control means is preprogrammed with a plurality of thawing protocols in encoded form and includes means for automatically selecting from among said thawing protocols in accordance with specimen type.

20. A method for storing a perishable specimen, comprising the steps of:
(a) inserting the specimen in a first chamber having a first temperature;
(b) maintaining said specimen for at least a first predetermined period in said first chamber;
(c) automatically moving said specimen, upon termination of said first predetermined period from said first chamber to a second chamber having a second temperature;
(d) maintaining said specimen for an indeterminate period in said second chamber;
(e) subsequent to the termination of said indeterminate period, automatically moving said specimen from said second chamber back to said first chamber;
(f) upon shifting of said specimen from said second chamber to said first chamber, maintaining said specimen for at least a second predetermined period in said first chamber; and
(g) removing said specimen from said first chamber upon termination of said second predetermined period.

21. The method according to claim 20 wherein said first temperature is lower than room temperature and said second temperature is lower than said first temperature.

22. The method according to claim 21, further comprising the step of at least partially automatically determining said first predetermined period in accordance with a pre-established freezing protocol for said specimen.

23. The method according to claim 22, further comprising the step of at least partially automatically selecting said pre-established freezing protocol from a plurality of freezing protocols stored in encoded form in a computer memory, said step of automatically selecting from among said freezing protocols being implemented in accordance with specimen type.

24. The method according to claim 21, further comprising the step of at least partially automatically determining said second predetermined period in accordance with a pre-established thawing protocol for said specimen.

25. The method according to claim 24, further comprising the step of at least partially automatically selecting said pre-established thawing protocol from a plurality of thawing protocols stored in encoded form in a computer memory, said step of automatically selecting from among said thawing protocols being implemented in accordance with specimen type.

* * * * *